US012788594B2

(12) United States Patent
Eder et al.

(10) Patent No.: US 12,788,594 B2
(45) Date of Patent: Nov. 10, 2026

(54) PROSTHETIC FINGER AND PROSTHETIC HAND HAVING A PROSTHETIC FINGER

(71) Applicant: OTTO BOCK HEALTHCARE PRODUCTS GMBH, Vienna (AT)

(72) Inventors: Florian Eder, Vienna (AT); Josef Gürtl, Vienna (AT); Christoph Ledinger, Vienna (AT)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 321 days.

(21) Appl. No.: 18/715,422

(22) PCT Filed: Dec. 1, 2022

(86) PCT No.: PCT/EP2022/084047
§ 371 (c)(1),
(2) Date: May 31, 2024

(87) PCT Pub. No.: WO2023/104630
PCT Pub. Date: Jun. 15, 2023

(65) Prior Publication Data
US 2025/0025318 A1 Jan. 23, 2025

(30) Foreign Application Priority Data
Dec. 8, 2021 (DE) ..................... 10 2021 132 277.4

(51) Int. Cl.
*A61F 2/58* (2006.01)
*A61F 2/50* (2006.01)
*A61F 2/70* (2006.01)

(52) U.S. Cl.
CPC ...... *A61F 2/586* (2013.01); *A61F 2002/5072* (2013.01); *A61F 2002/701* (2013.01)

(58) Field of Classification Search
CPC .............. A61F 2/586; A61F 2002/5072; A61F 2002/701; A61F 2002/587
See application file for complete search history.

(56) References Cited

U.S. PATENT DOCUMENTS 6,424,886 B1 * 7/2002 Iversen ..................... A61F 2/54 403/321
6,896,704 B1 * 5/2005 Higuchi .................. A61F 2/586 623/64
(Continued)

FOREIGN PATENT DOCUMENTS

DE 10 2005 061 313 A1 8/2007
DE 10 2008 056 520 A1 6/2010
(Continued)

*Primary Examiner* — Nitin Patel
(74) *Attorney, Agent, or Firm* — WCF IP

(57) ABSTRACT

The invention relates to a prosthetic finger which is associated with a motor drive (5) by means of which the prosthetic finger (101) can pivoted relative to a chassis (100) about a first pivot axis (2), the prosthetic finger having a finger element (3) which is pivotably mounted on the chassis (100) about the first pivot axis (2) and which is coupled to a support (19), the support (19) is coupled to a drive element (17) which can be coupled to the motor drive (5) and which is torque-transmittingly coupled to the support (19), wherein the drive element (17) is torque-transmittingly coupled to the support (19) via a coupling element (18), wherein the coupling element (18) is axially displaceably mounted on the support (19) and resiliently preloaded in the direction of the drive element (17).

17 Claims, 8 Drawing Sheets

(56) References Cited

U.S. PATENT DOCUMENTS

| | | | | |
|---|---|---|---|---|
| 8,491,666 | B2 | 7/2013 | Schulz | |
| 9,974,667 | B1 * | 5/2018 | Cazenave | A61F 2/586 |
| 11,246,721 | B2 * | 2/2022 | Sensinger | A61F 2/583 |
| 2008/0262636 | A1 | 10/2008 | Puchhammer | |
| 2016/0235554 | A1 | 8/2016 | Iversen et al. | |
| 2016/0250044 | A1 | 9/2016 | Iversen et al. | |
| 2021/0251779 | A1 * | 8/2021 | Hunter | A61F 2/583 |
| 2022/0346979 | A1 * | 11/2022 | Cornman | A61F 2/586 |
| 2024/0299195 | A1 * | 9/2024 | Perry | A61F 2/54 |
| 2025/0288434 | A1 * | 9/2025 | Cornman | A61F 2/586 |

FOREIGN PATENT DOCUMENTS

| | | | |
|---|---|---|---|
| EP | 2 653 137 | A1 | 10/2013 |
| EP | 2 125 091 | B1 | 4/2016 |

* cited by examiner

PROSTHETIC FINGER AND PROSTHETIC HAND HAVING A PROSTHETIC FINGER

The invention relates to a prosthetic finger which is assigned a motor drive via which the prosthetic finger is pivotable relative to a chassis about a first pivot axis, having a finger element which is mounted on the chassis pivotably about the first pivot axis and is coupled to a carrier, the carrier being coupled to a drive element which can be coupled to the drive and is coupled to the carrier in a torque-transmitting manner. The invention also relates to a prosthetic hand having a prosthetic finger which is mounted on a chassis of the prosthetic hand.

Prosthetic fingers and prosthetic hands replace fingers or hands that are missing or that have been lost. The prosthetic fingers and the prosthetic hands simulate the human anatomy. Prosthetic hands generally have four prosthetic fingers which, in the region of connection to the chassis, are mounted pivotably about pivot axes oriented substantially parallel to each other. The prosthetic fingers may have further distal pivot axes, oriented substantially parallel thereto, on the finger elements in order to be able to form a fist. Prosthetic hands also have a thumb, which is also considered a finger. The thumb is an essential part of the human hand, making it a universal tool that has a large number of possible movements and degrees of freedom. The importance of the thumb lies particularly in the fact that its position relative to the other fingers is critical for different grip patterns. Important positions and attitudes are the opposition grip and the lateral grip. In the opposition grip, large objects can be held and smaller objects can be gripped.

The lateral grip is especially useful for flat objects, but it is also used when placing the hand flat on a table, when gripping a computer mouse and the like.

The basal joint of the thumb of a natural hand takes the form of a saddle joint. In the case of prosthetic hands, the positions that can be achieved with them are often obtained by a combination of pivot joints, which allow the base of the thumb to pivot about pivot axes oriented at an angle to each other. A first pivot joint about a first pivot axis controls the flexion and extension of the finger element of the thumb, by which objects can be gripped and let go. The finger element is moved in the palmar direction. The other joint allows an abduction and adduction of the thumb, by which different types of grip, such as the opposition grip and the lateral grip, can be achieved. The finger element of the thumb is moved to the respective opposition position or lateral position.

Active movements of prostheses are often controlled and initiated via myoelectric signals. In this case, electric signals generated in muscle cells are detected via electrodes and are transmitted to a control device which activates or deactivates a motor drive after processing the signals and, if necessary, amplifying them. The energy for the adjustment is provided via an energy storage device, in particular an accumulator. In order to achieve sufficiently high forces and speeds, the motor drive is coupled to the prosthetic finger via downstream gear stages, if necessary. Each movement of a prosthetic finger consumes energy, which must be taken from the energy storage device, with only a limited energy supply being present in the energy storage device. A prosthetic hand with a drive is described in EP 2 125 091 B1, for example.

A passive movement of the prosthetic finger or of a prosthetic hand is present when, by the action of external forces, the prosthetic fingers are moved relative to the chassis or the prosthetic hand as such is moved. Such movements are performed consciously, for example, by the contralateral hand of the prosthesis wearer or by the application of compressive forces or tensile forces when using the prosthetic hand.

Passive movements do not consume energy from the energy storage device. If the prosthetic hand or a prosthetic finger is mounted elastically, a return to a starting position takes place after an external force ceases. By means of latching elements, it is possible that, after a passive movement, the prosthetic finger or the prosthetic hand is maintained in a certain position, for example to hold a prosthetic finger in an applied or spread position.

US 2016/0 250 044 A1 relates to a toothed wheel locking mechanism for a hand prosthesis having a first internal toothed wheel and a second internal toothed wheel. The first internal toothed wheel is attached to a distal finger component of a finger element. The second internal toothed wheel is attached to a proximal finger component of the finger element. An external toothed wheel is coupled to a knob and forms a bridge between the first internal toothed wheel and the second internal toothed wheel, in order to lock a joint of the finger element. A spring is designed to return the knob to a locked position.

DE 10 2008 056 520 A1 relates to a finger element having a carrier component, a first finger link having a first joint connection to the carrier component and a second finger link having a second joint connection to the first finger link. A coupling mechanism is arranged between the first and the second joint connection. An actuator for the first joint connection has a motor with a drive shaft and a worm gear with a threaded worm and with a tooth segment engaging the threaded worm. The threaded worm is mounted axially movably and with form-fit engagement on the drive shaft and is guided axially through separate guides.

The object of the present invention is to make available a prosthetic finger and a prosthetic hand that can be used for longer and without having to charge an energy storage device.

This object is achieved by a prosthetic finger or a prosthetic hand having the features of the independent claims. Advantageous embodiments and developments of the invention are disclosed in the subclaims, the description and the figures.

In the prosthetic finger, which is assigned a motor drive via which the prosthetic finger is pivotable relative to a chassis about a first pivot axis, having a finger element which is mounted on the chassis pivotably about the first pivot axis and is coupled to a carrier, the carrier being coupled to a drive element which can be coupled to the drive and is coupled to the carrier in a torque-transmitting manner, provision is made that the drive element is coupled to the carrier in a torque-transmitting manner via a coupling element, wherein the coupling element is mounted on the carrier to be axially displaceable and elastically pretensioned in the direction of the drive element. The prosthetic finger is designed in particular as a prosthetic thumb, wherein the finger element can have a multi-component design, in particular a two-component design, such that a distal component, analogously to a natural finger or thumb, is mounted pivotably on a proximal component. In the case of a thumb, the first pivot axis permits in particular an abduction and adduction and thus a rotation of the finger element about a pivot axis that is oriented substantially in the longitudinal extent of the prosthetic hand and extends from a wrist to the fingertips. In the case of use for a finger, the first pivot axis preferably extends perpendicular to the longitudinal extent of the finger element, i.e. perpendicular to the proximal-distal orientation. The finger element is coupled to a carrier and can be mounted directly on the carrier, for example pivotably thereon, or can be coupled to the carrier via a gearing or a coupling element, such that the pivotable bearing is realized via a bearing point, for example, on the chassis. The carrier itself is coupled to a drive element. In particular, the drive element is mounted on the carrier and fastened, the drive element being able to be coupled to the drive, and being coupled thereto in the assembled state of the prosthetic hand. The drive, in particular as an electromotive drive, engages with the drive element and drives the latter, the drive element in turn being coupled to the carrier in such a way that the force or the torque from the drive is transferred to the carrier. The coupling is effected in this case via a coupling element, which in turn is coupled to the carrier in a torque-transmitting manner, in particular connected or coupled to the carrier directly by a form fit or via one or more intermediate elements. The coupling element is mounted on the carrier in a manner axially movable along the longitudinal extent of the carrier and is elastically pretensioned in the direction of the drive element. Besides active adjustment by the drive, it is thereby possible that the carrier and thus the entire prosthetic finger can also be adjusted passively by a user or, during use, by externally acting forces. In particular, abduction and adduction, with appropriate orientation, and pivoting about the first pivot axis are possible both actively and passively. The coupling element does not influence the active adjustment by the drive via the elastic pretensioning in the direction of the drive element, and therefore, during a passive adjustment, no energy is consumed, in particular no stored electrical energy. At the same time, during an active adjustment by the motor drive, a holding force or a restoring force due to an elastic element does not have to be overcome, and therefore the active operation of the prosthetic finger can be optimized in terms of energy consumption.

In one embodiment, the drive element is designed as a toothed wheel or toothed wheel segment and has latching elements and/or friction regions on the end face, i.e. not on the circumference of the toothed wheel or toothed wheel segment. The coupling element also has latching elements and/or friction regions and is designed as a latching disk, wherein the latching elements and/or friction regions are designed correspondingly to the front-end latching elements and/or friction regions of the drive element. The design of the drive element and of the coupling element as latching disks permits defined latching positions of the drive element relative to the coupling element, and thus also defined positions of the prosthetic finger relative to the chassis. The positioning via latching elements does not affect the active drivetrain with the motor drive, as long as an adjustable resistance moment is not exceeded. The resistance moment arises from the elastic pretensioning of the coupling element in the direction of the drive element, and also from the geometric configurations of the latching elements and/or the friction properties of the friction regions. On account of the latching and the preferably uniform spacing of the latching elements in the circumferential direction, the user can quickly pivot the prosthetic finger passively, in particular the thumb, or pivot it to the side, for example in order to lay the prosthetic hand flat on a table.

In one embodiment, the latching elements on the drive element and the correspondingly designed latching elements on the coupling element are configured as a crown gear with helical tooth flanks. The design of the tooth flanks in the form of screw surfaces permits surface contact over the entire locking process. As a result, the maximum surface pressures in the contact region between the tooth flanks can be reduced, whereby the overall structure can be significantly reduced while maintaining the same strength or the same transmissible moments.

In order to facilitate the passive adjustment, the latching elements are inclined or beveled in at least one circumferential direction; the latching elements are preferably beveled or inclined in both circumferential directions. The bevels or inclines can be rectilinear or curved, so that teeth or undulations form on the respective end faces of the drive element and of the coupling element.

The drive element and the coupling element are preferably provided with a crown toothing and are of rotationally symmetrical construction at least in partial regions. The carrier has, for example, a pin on which the coupling element is mounted with form-fit engagement and in a torque-transmitting manner. For this purpose, a toothing or another form-fit device is arranged or formed on the outside of the carrier, with which an axially mobility of the coupling element is ensured and at the same time a torque can be transmitted, so that the carrier can be pivoted about the first pivot axis.

The carrier is mounted pivotably about the first pivot axis, wherein the finger element is coupled to the carrier for conjoint rotation with respect to the axis. As a result, a rotation of the carrier about the axis leads to a rotation of the spring element either about this axis or about the pivot axis of the finger element.

In one embodiment, the finger element is mounted pivotably on the carrier, which is particularly advantageous when the carrier itself is pivotable relative to the chassis. This allows the finger elements or prosthetic fingers to be positioned better and more flexibly, in order to be able to realize different types of grip and to better grip objects.

In one embodiment, the finger element is mounted pivotably on the carrier about the first pivot axis, which has the effect that a passive movement about the first pivot axis is permitted via the elastically pretensioned coupling element. The pivoting about the second pivot axis can likewise be afforded a possibility of passive pivoting.

In one embodiment, the finger element is coupled to the carrier via a toothed wheel or a toothed wheel segment, so that a gear ratio is formed at the same time. A component of the gearing is the drive element that acts on the carrier. A torque or a rotational movement is transmitted, by a toothed wheel arranged or formed on the carrier, to a toothed wheel segment or an entire toothed wheel which is arranged, formed or secured on the finger element.

It is also possible for further gear stages or toothed wheel stages to be arranged or formed between the carrier and the finger element in order to transmit a corresponding rotational movement of the carrier to the finger element.

In one embodiment, the elastic pretensioning of the coupling element in the direction of the drive element is effected via a spring, an elastomer element and/or a disk spring or a combination of disk springs.

In one embodiment, the finger element is mounted on a holder pivotably about a second pivot axis, the holder being secured on the carrier. Together with the carrier, the holder and thus also the finger element pivot when the carrier is pivoted about the first axis. Independently of a pivoting movement about the first axis, the finger element can be moved about the second pivot axis, either passively or, in one embodiment, actively. For this purpose, a drive is provided which is mounted in or on the finger element and via which the finger element is mounted on the holder pivotably by motor about the second pivot axis.

The first pivot axis and the second pivot axis are not parallel and not collinear to each other, but in a cross, although the pivot axes do not have to intersect. The pivot axes can also be skewed with respect to each other and do not cross each other.

In one embodiment, the drive element is mounted freely rotatably on the carrier and effects only the rotation of the coupling element and thus a transmission of force to the carrier, when the coupling element bears with a sufficient contact force on the drive element and transmits torques positively and/or frictionally.

The coupling element is loaded in the direction of the drive element with a pretensioning force sufficient to transmit a torque to the carrier. However, the transmission of the torque takes place only up to a certain previously defined and advantageously adjustable load limit. If the resistance to displacement becomes too great or the applied torque becomes too great, the carrier decouples itself from the coupling element by moving axially relative to the carrier. This provides both overload protection and passive adjustability.

In one embodiment, provision is made that the carrier is assigned a position sensor or a marker via which the position of the carrier relative to the chassis is detected. The information concerning the position of the carrier and thus also of the prosthetic finger relative to the chassis is important in order to ascertain, in the case of a subsequent adjustment command by the user via myoelectric signals, in which starting position the prosthetic finger is located, so that the necessary adjustment distance is calculated from this. For example, if the prosthetic finger is passively adjusted and is in a latching position, the finger is not in the correct position when a closure command is issued, and it cannot be moved to the desired or necessary position via the drive. The position sensor prevents incorrect operation. When, by a combination of muscle contractions, the user generates a defined closure signal by which the prosthetic hand is intended to be brought into a defined end position, for example a lateral grip, the control system calculates the required adjustment distance for the respective prosthetic finger based on the existing position signals. This ensures that a correct end position is reached upon each command, irrespective of the current position of the prosthetic finger relative to the chassis.

The drive is designed in particular as an electric motor, which in turn drives an output element, for example a toothed wheel or a worm screw, which in turn engages with the drive element in an assembled state of the prosthetic hand.

The drive can be coupled to the output element via a gearing and/or a coupling. The drivetrain from the motor drive, which is mounted in particular in the chassis, to the coupling element is advantageously self-locking, so that no forces are transmitted to the drive upon loading of the prosthetic finger and/or of the carrier. Self-locking also ensures that no energy has to be expended in order to maintain the adopted position.

In addition to the possibility of simple and quick adjustment to different latched positions without the use of electrical energy, the described embodiment also permits an overload protection for the motor in the event of unforeseen blocking of the adjustment of the finger element by an obstacle or the like.

An exemplary embodiment of the invention is explained in more detail below on the basis of the figures. Which reference signs denote identical components. In the drawing.

Figure 1:
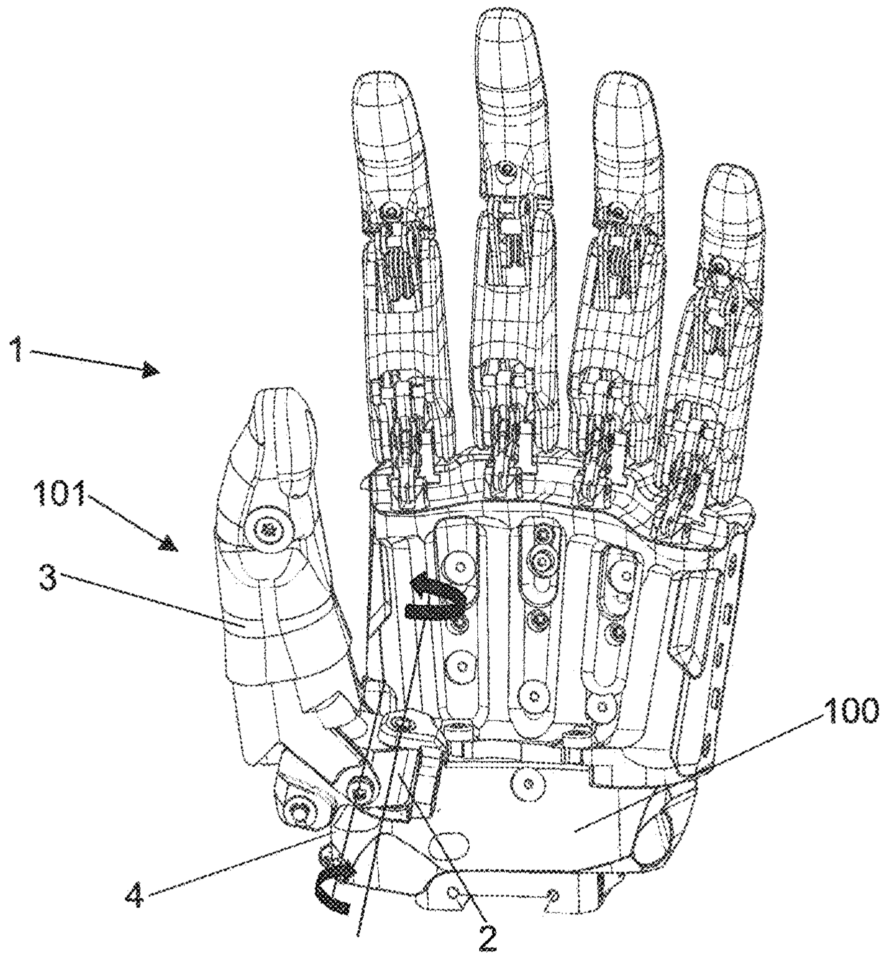
FIG. 1 shows a perspective view of a prosthetic hand.

FIG. 1 shows a prosthetic hand 1 having a chassis 100 and a prosthetic finger 101. The prosthetic finger 101 is designed as a prosthetic thumb. In addition, four further prosthetic fingers are articulated and driven on the chassis 100. The prosthetic fingers have a basal joint, which connects a proximal finger component to the chassis in an articulated manner. A distal finger component is articulated on the proximal finger component and is moved either individually or in combination with the proximal finger component. Drives (not shown in detail) within the chassis allow each finger to be moved individually or all fingers to be moved together in order to perform flexion in the direction of the palm of the hand or extension to the stretched position shown. The prosthetic finger 101 as a prosthetic thumb is pivotable relative to the chassis about two axes 2, 4. A first axis 2, explained in more detail below, permits abduction and adduction, while the second axis 4 permits flexion in the direction of the palm of the hand or the other prosthetic fingers. The prosthetic thumb also has a two-component finger element 3, having a proximal finger component and a distal finger component. Similarly to what is described for the other prosthetic fingers, the distal finger component is mounted pivotably on the proximal finger component. A drive, explained in more detail below, is mounted inside the chassis 100 and designed as an electric motor. An energy storage device and a control device are either arranged within the prosthetic hand 1 or are located in proximal prosthesis components, for example a forearm socket.

Figure 2:
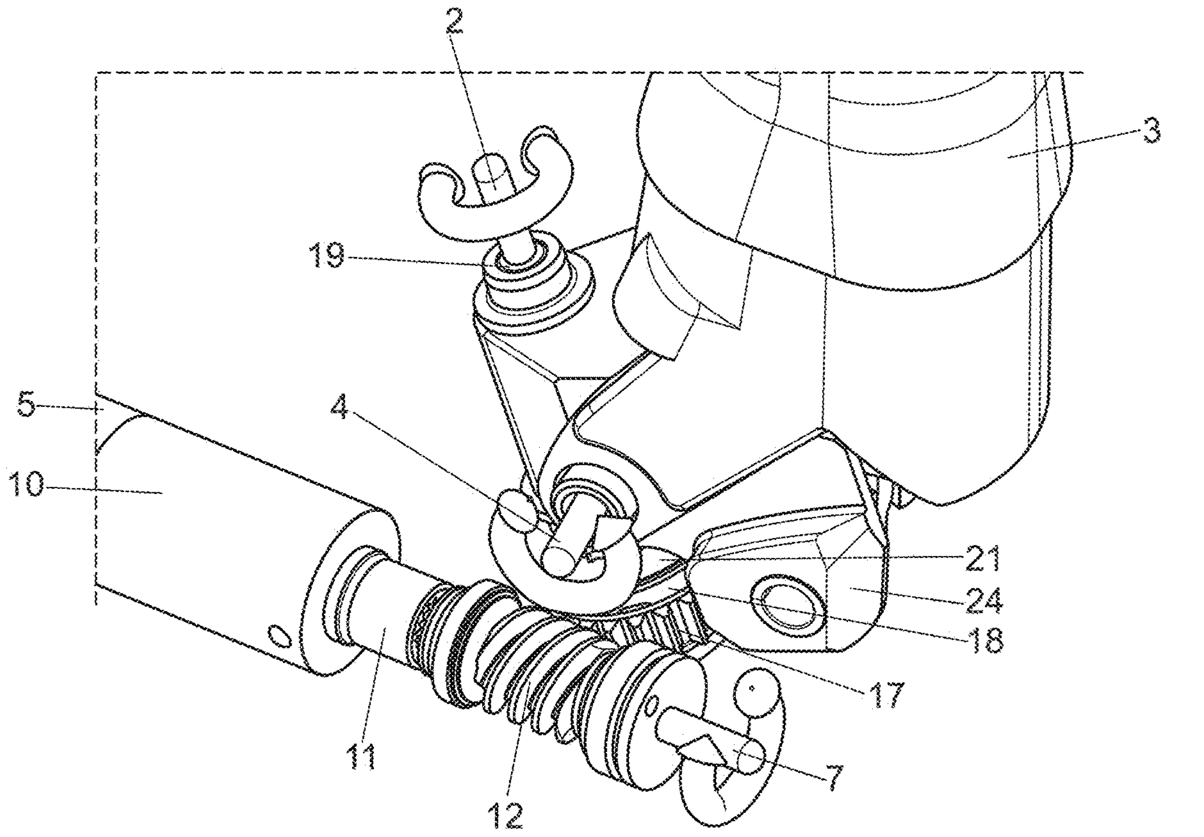
FIG. 2 shows a schematic detailed view of the drive.

FIG. 2 shows part of the finger element 3, namely the proximal finger component, which is mounted pivotably about the first pivot axis 2. Pivoting about the first pivot axis 2 takes place via a holder 24, on which the finger element 3 is mounted pivotably about the second pivot axis 4. The two pivot axes 2, 4 are at an angle to each other but do not intersect. In principle, it is also possible for the two axes 2, 4 to intersect. The rotation about the first axis 2 is effected via a drive 5, which is designed as an electric motor and drives an output element 12 via a gearing 10, in the form of a planetary gear, and a coupling 11. The output element 12 is designed as a worm screw that rotates about a rotation axis 7. On both sides of the output element 12, thrust washers and bearing parts are arranged to support the output element 12 in the chassis 100. The teeth of the output element 12 engage in a worm gear as drive element 17 and rotate the latter in one direction or the other about the pivot axis 2, depending on the direction of rotation of the electric motor 5. The drive element 17 is in turn connected to a coupling element 18 by reversible form-fit engagement, as will be explained in more detail below. For this purpose, spring elements 21 are arranged above the coupling element and are supported on a projection of a carrier 19. The carrier 19 in turn is coupled to the holder 24 for conjoint rotation and pivots the finger element 3 when the carrier 19 is rotated about the first pivot axis 2.

Figure 3:
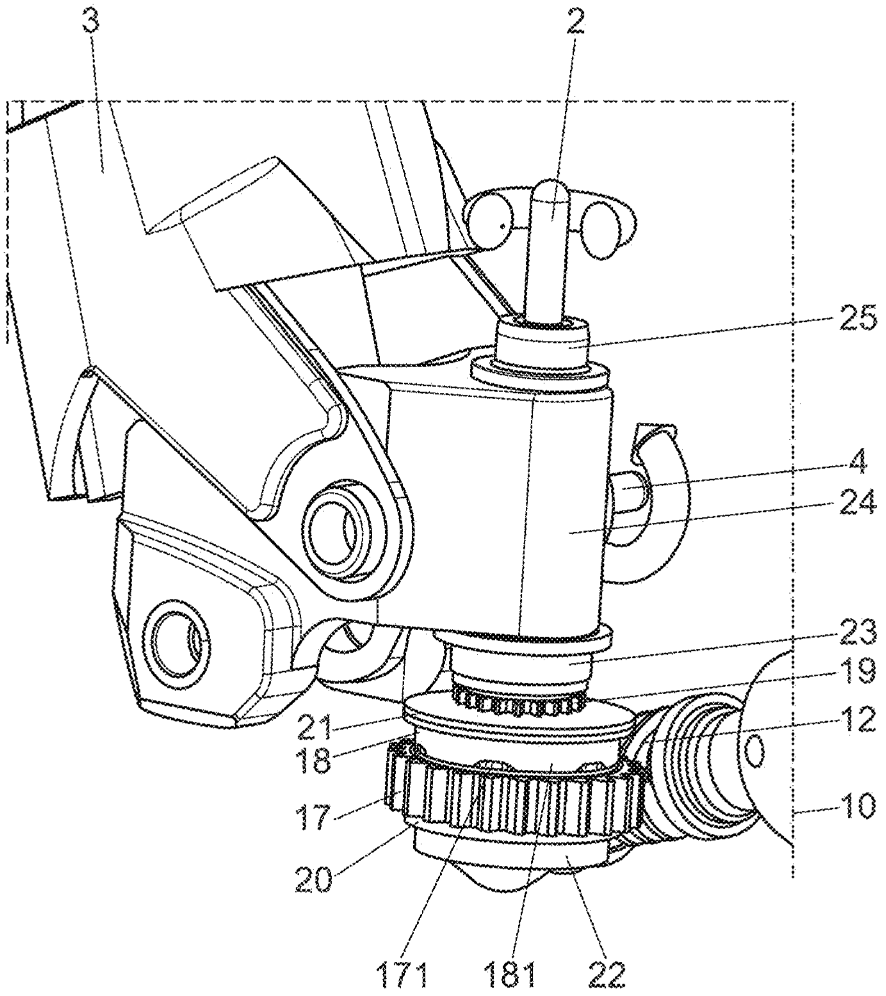
FIG. 3 shows a detailed view from another perspective.

FIG. 3 shows an exposed structure of the components from FIG. 2 in another perspective. When the worm screw 2 is driven, the drive element 17 rotates about the pivot axis 2. The drive element 17 is supported at the bottom on a clamping element 20; below the clamping element 20 a magnetic ring 22 is arranged which serves as a signal transmitter for a position sensor (not shown) in the chassis 100. The drive element 17 has, at the upper end face, latching elements 171 or form-fitting elements, which are distributed about the circumference at the end face. The distribution is advantageously uniform about the circumference. Above the drive element 17, the coupling element 18 is form-fittingly connected to the latching elements 171, since the underside of the coupling element 18 is designed correspondingly to the top of the drive element 17.

The coupling element 18 is mounted on the carrier 19 axially movably along the longitudinal extent of the first pivot axis 2. A movement is impeded by the spring element 21 in the form of a disk spring pack. On the inside of the coupling element 18, an internal toothing is formed, which is designed correspondingly to an external toothing on the carrier 19. The internal toothing of the coupling element 18 engages in the external toothing of the carrier 19 and causes the carrier 19 to be moved about the first pivot axis 2 when the drive element 17 is rotated. The carrier 19 is mounted torque-transmittingly or for conjoint rotation in the holder 24, which in turn has two bearing elements 23, 25, with which the holder 24 is mounted in the chassis 100. The second pivot axis 4, about which the finger element 3 can be pivoted in the palmar direction for gripping, is formed on the holder 24.

Figure 4:
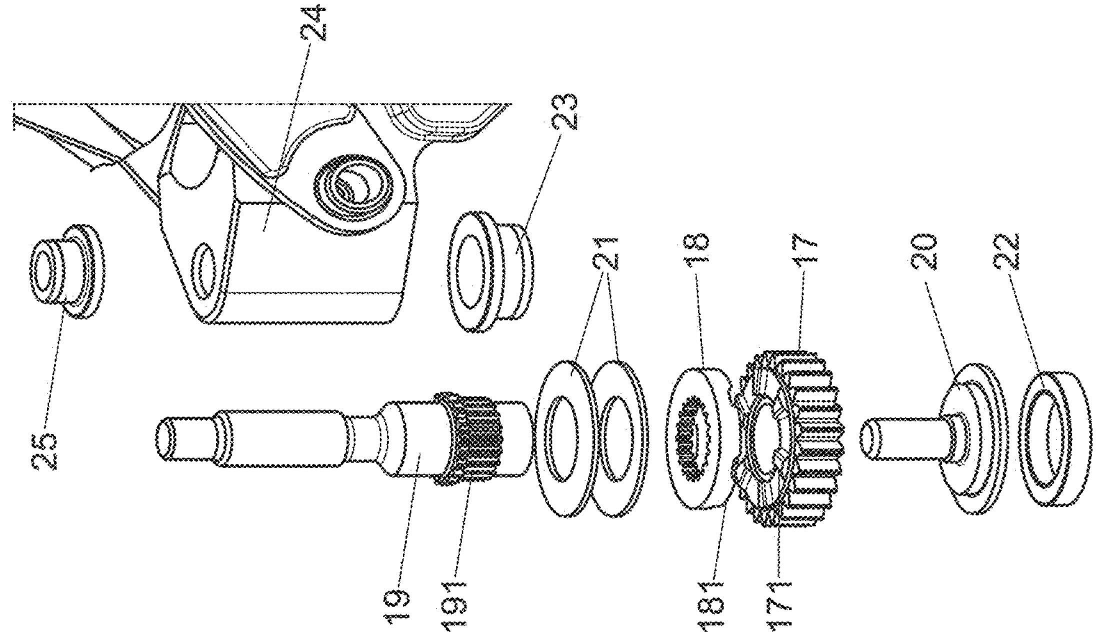
FIG. 4 shows an exploded view of a part of the prosthetic finger.

It will be seen from FIG. 3 and better still from FIG. 4 that the latching elements 171 on the drive element 17 are designed in both circumferential directions with run-on ramps or bevels, and the corresponding latching elements 181 of the coupling element 18 likewise have run-on ramps or bevels. When the motor drive 5 is activated, the output element 12 rotates about the rotation axis 7 and drives the drive element 17. The drive element 17, otherwise mounted freely rotatably on the carrier 19, is connected via the latching elements 171 and 181 to the coupling element 18 in a torque-transmitting manner. The coupling element 18 as a latching disk is coupled to the carrier 19 for conjoint rotation via a toothing 191, such that a rotation of the drive element 17 leads to a rotation of the carrier 19. On account of the holder 24 being mounted on the carrier 19 for conjoint rotation, the finger element 3 is also pivoted together with the holder 24 about the first pivot axis 2. As soon as a resistance to pivoting about the first pivot axis 2 arises, for example because an end position is reached or the prosthetic finger 101 is pressed against an object, a relative movement can take place between the drive element 17 and the coupling element 18. On account of the beveled design of the latching elements 171, 181, a rotation is possible with simultaneous axial displacement of the coupling element 18 upward along the longitudinal extent of the first pivot axis 2. This takes place counter to the pretensioning force applied by the spring elements 21. If the applied torque is too great to be transmitted from the positive and frictional connection between the drive element 17 and the coupling element 18 to the carrier 19, the coupling element 18 is raised until its underside rests on the top of the latching element 171 of the drive element 17 and slips through. This provides an overload protection, for example.

To effect a passive adjustment of the finger element 3 or of the prosthetic finger about the first pivot axis 2, a torque about the first pivot axis 2 is applied via the holder 24 or the finger element 3. The drivetrain from the motor drive 5 via the output element 12 to the drive element 17 is designed to be self-locking, such that the drive element 17 does not drive the output element 12 when torque is applied. The holder 24 with the carrier 19 then rotates relative to the drive element 17. On account of the carrier 19 and the coupling element 18 being coupled in a form-fitting manner and for conjoint rotation, this leads to an upward axial displacement of the coupling element 18 counter to the pretensioning of the spring elements 21, until a next latching position is reached.

The spring elements 21 ensure the force-fit and form-fit connection of the drive element 17 and the coupling element 18 up to a limit torque. Above the limit torque, the coupling element 18 or the latching disk moves axially on the carrier 19 along the longitudinal extent of the first pivot axis 2 until the maximum height of the latching elements 171 is reached. At a further applied torque, the coupling element 18, together with the carrier 19 and the holder 24 secured thereon and the prosthetic finger 101, moves to the next latching position.

It will be seen from FIG. 4 that a total of six latching elements 171 or latches are arranged or formed on the upper end face of the drive element 17. Thus, the carrier 19 with the holder 24 and the prosthetic finger can be moved to six latching positions, since six recesses are also present at the underside of the coupling element 18. With a different division or a greater or smaller number of latching elements 171, 181 or latches, different numbers of latching positions are possible. It will be seen from FIG. 4 that the coupling element 18 has an internal toothing which is designed correspondingly to an external toothing 191 of the carrier 19. The spring elements 21 are supported on the top of the coupling element 18 on the one hand and on a shoulder 192 of the external toothing 191 on the other hand on the carrier 19 and, in the assembled state, bring about a pretensioning of the coupling element 18 in the direction of the drive element 17.

Figure 5:
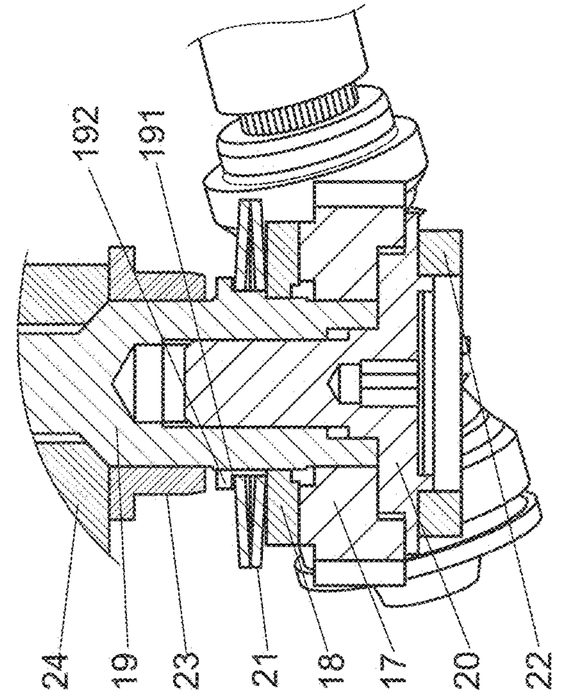
FIG. 5 shows a sectional view through an arrangement from FIG. 3.

FIG. 5 shows a sectional view of the assembled state according to FIG. 3. The clamping element 20 has an external thread, which is screwed into an internal thread inside the carrier 19. The clamping element 20 provides an axial support for the drive element 17 freely rotatable about the outer circumference of the carrier 19. In the outer circumference of the clamping element 20, a magnetic ring 22 is arranged which serves as a marker or as a positioning aid to define an orientation of the magnetic field and thus the actual position of the prosthetic finger 101 relative to the chassis 100.

The coupling element 18 above the drive element 17 is pretensioned with respect to the drive element 17 via the two disk springs of the spring element 21, which bear on the shoulder 192 of the external toothing 191. The holder 24 is clamped or screwed or mounted in other ways on the carrier 19 above the toothing 191 in a rotationally fixed manner.

Figure 6:
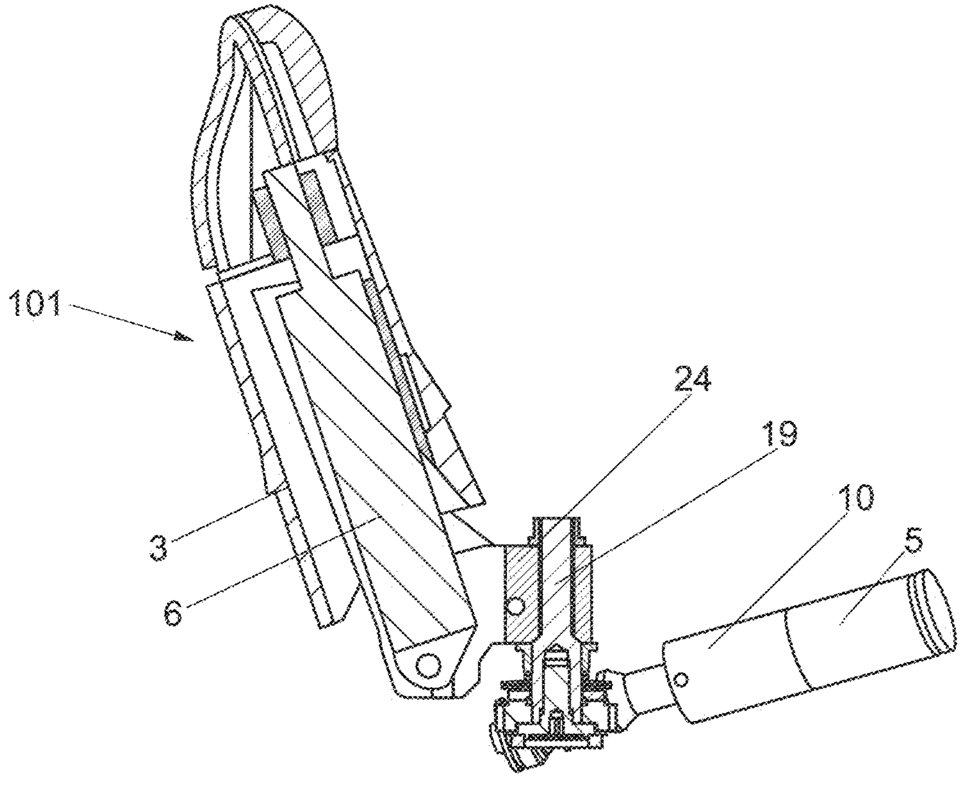
FIG. 6 shows a sectional view through a prosthetic finger.

FIG. 6 shows a cross section through the prosthetic finger 101 with a drive 6 arranged within the finger element 3 for actuating and pivoting the finger element 3 about the second pivot axis 4, such that opening and closing of the thumb can take place independently of an abduction or adduction of the thumb about the first pivot axis 2.

Figure 7:
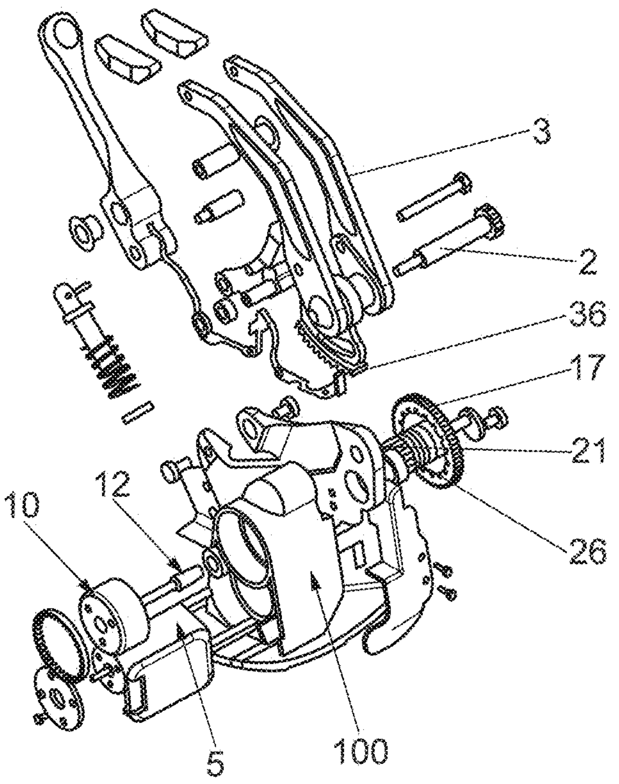
FIG. 7 shows an exploded view of a variant.

FIG. 7 shows a variant in which the finger element 3 is mounted on the chassis 100 pivotably about a first pivot axis 2. A motor drive 5 is mounted inside the chassis 100 and provided with an output element 12 via a gearing 10. The output element 12 is a toothed wheel on a shaft, which toothed wheel engages with the drive element 17. The basic structure of the drive element 17 with the coupling element 18, which cannot be seen in this view, with the carrier 19 and with the spring element 21 corresponds to the structure of the embodiment according to FIGS. 2 to 6. A toothed wheel 26 is mounted for conjoint rotation on the carrier 19 and engages in a toothed wheel segment 36, which is arranged on, formed on or secured on the finger element 30. By way of the toothed wheel segment 36, the finger element 3 is moved in one direction or the other about the first pivot axis 2 on the chassis 100 when the toothed wheel 26 is rotated.

Figure 8:
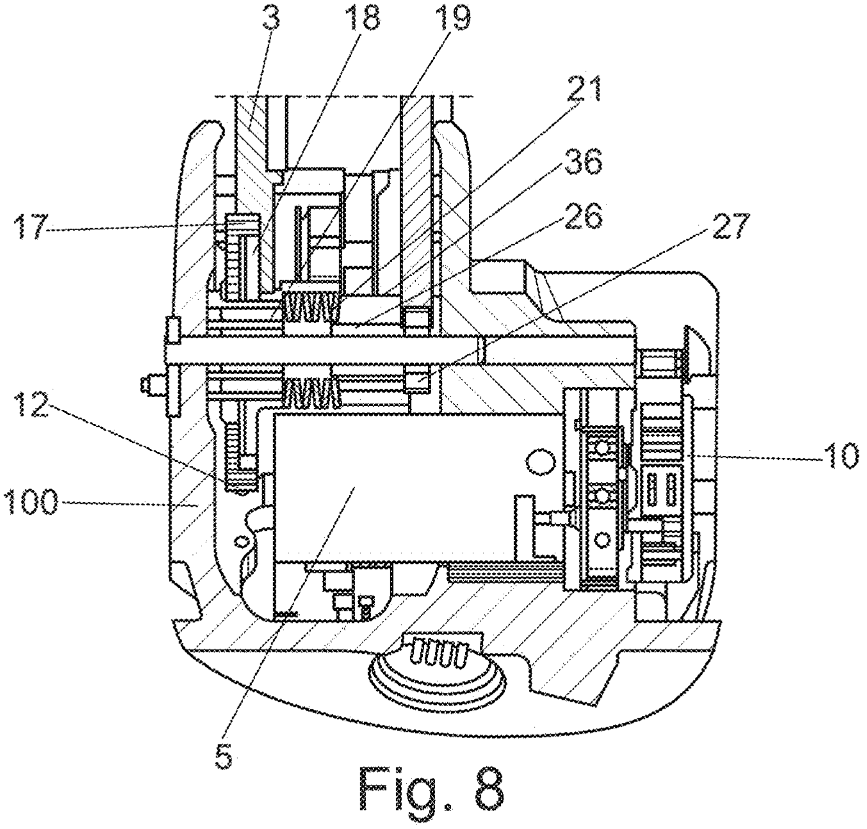
FIG. 8 shows a detailed sectional view of FIG. 7.
Figure 10:
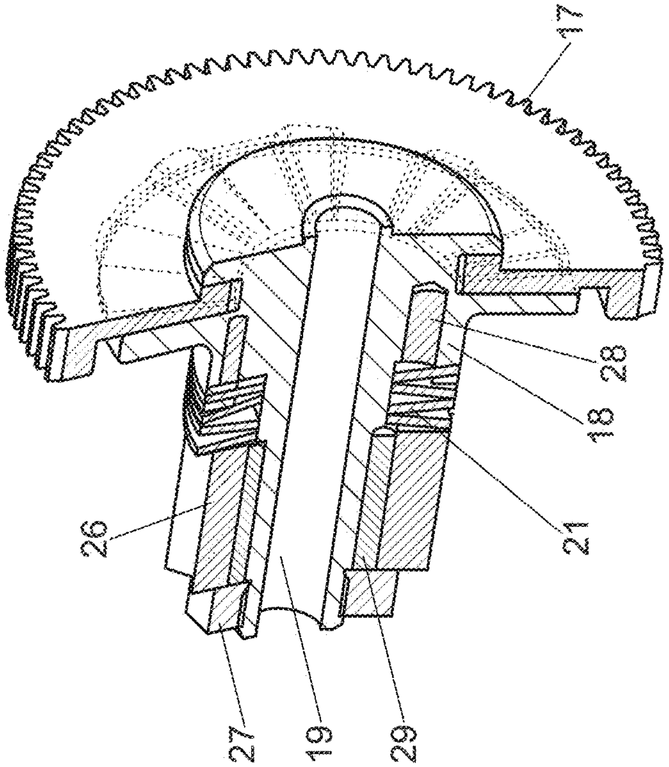
FIG. 10 shows a sectional view of a detail of FIG. 8.

FIG. 8 shows the chassis 100 in a cross-sectional view from another perspective, with the motor drive 5 arranged therein and with the gearing 10 via which the output element 12 is driven. The output element 12 as a toothed wheel engages in the drive element 17, which is mounted rotatably on the carrier 19. The coupling element 18, with latching elements (not shown)

at the end face, is pressed against the drive element 17 by the spring element 21. The spring element 21 consists of a plurality of disk springs or disk spring packs and loads the coupling element 18 longitudinally or axially in the direction of the drive element 17. The coupling element 18 is mounted for conjoint rotation and axially displaceably on the carrier 19; the specific structure will be explained below. The spring element 21 is supported on the opposite side on the toothed wheel 26, which is likewise mounted on the carrier 19 for conjoint rotation and is axially secured by a nut 27. The spring pretensioning of the spring element 21 can be adjusted via the nut 27. The toothed wheel 26 meshes with the toothed wheel segment 36, which in turn is coupled to the finger element 3 torque-transmittingly or for conjoint rotation, such that a rotation of the toothed wheel 26 leads to a pivoting of the finger element 3 about the pivot axis 2.

Figure 9:
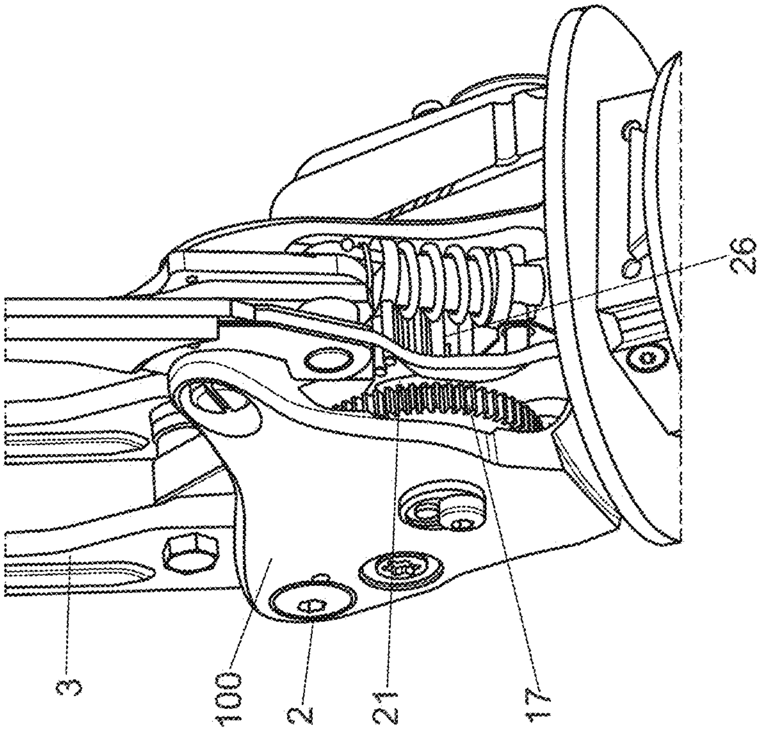
FIG. 9 shows a detailed perspective view of FIG. 7.
Figure 11:
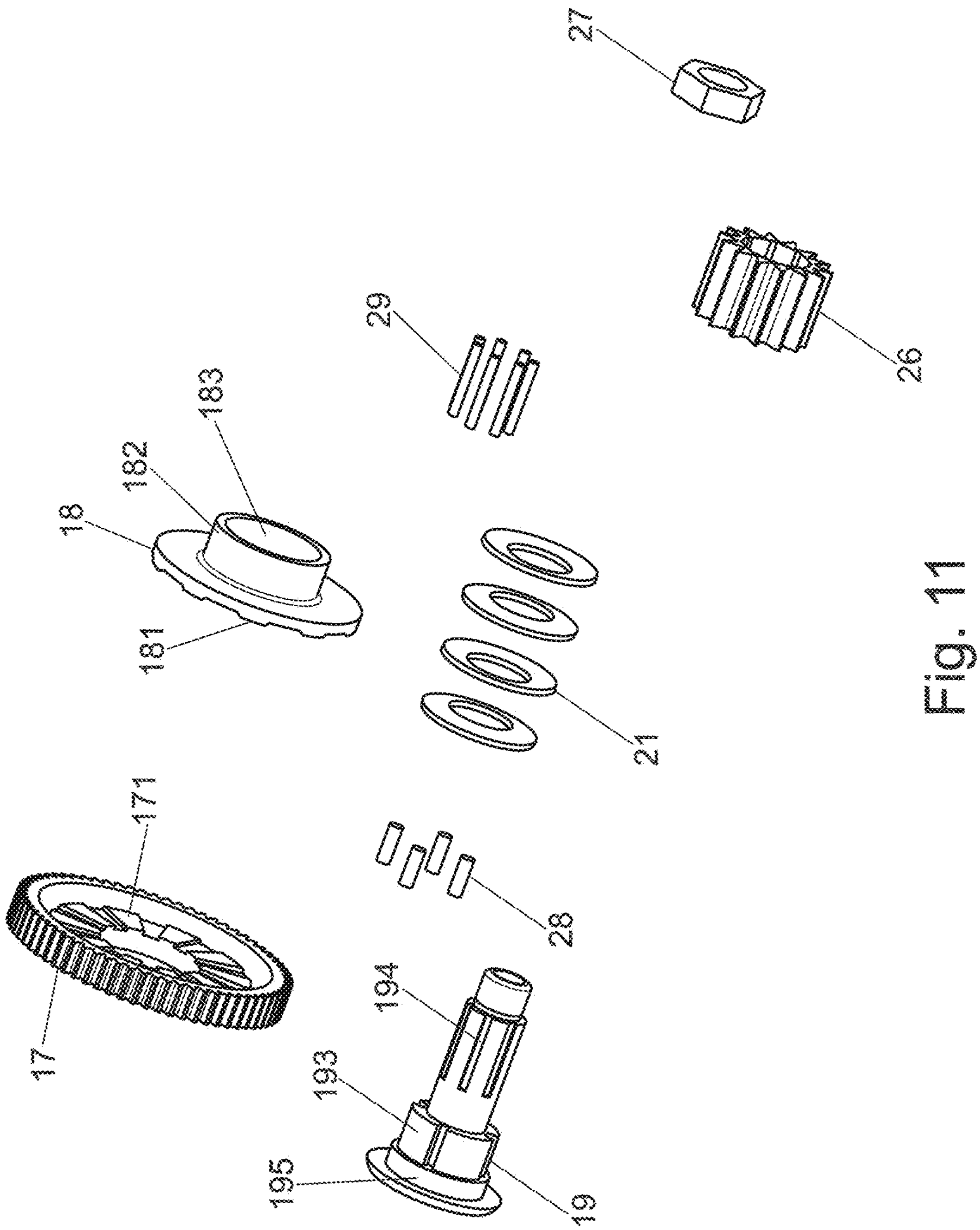
FIG. 11 shows an exploded view of components from FIG. 10.

FIG. 9 shows a detailed perspective view of the finger element 3 on the chassis 100. The finger element 3 is mounted on the chassis 100 about the first pivot axis 2. The motor and the gearing are likewise mounted inside the chassis 100. The drive element 17 can also be seen, which is coupled to the toothed wheel 26 via the coupling element (not visible), which is pressed by the spring element 21 onto the drive element 17, which toothed wheel 26 in turn drives the finger element 3.

The invention claimed is:

1. A prosthetic finger which is assigned a motor drive via which the prosthetic finger is pivotable relative to a chassis about a first pivot axis, comprising: having a finger element which is mounted on the chassis pivotably about the first pivot axis;

a carrier, wherein the finger element is coupled to the carrier; and a drive element coupleable to the motor drive, wherein the drive element is coupled to the carrier in a torque-transmitting manner via a coupling element, wherein the coupling element is mounted on the carrier so as to be axially displaceable and elastically pretensioned in a direction of the drive element wherein the drive element is designed as a toothed wheel or a toothed wheel segment, wherein the drive element comprises latching elements and/or friction regions at a front end, and wherein the coupling element is designed as a latching disk comprising—latching elements and/or friction regions which correspond to the latching elements and/or friction regions at the front end of the drive element.

2. The prosthetic finger as claimed in claim 1, wherein the drive element comprises latching elements and the latching disk of the coupling element comprises latching elements, and wherein both the latching elements of the drive element and the latching elements of the coupling element are inclined or beveled in at least one circumferential direction.

3. The prosthetic finger as claimed in claim 1 wherein the drive element comprises latching elements and the latching disk of the coupling element comprises latching elements, and wherein both the latching elements of the drive element and the latching elements of the coupling element are configured as a crown gear with helical tooth flanks.

4. The prosthetic finger as claimed in claim 1 wherein, characterized in that the coupling element is mounted on the carrier (19) with a form fit.

5. The prosthetic finger as claimed in claim 1 wherein the carrier is mounted pivotably about the first pivot axis, and the finger element is coupled to the carrier for conjoint rotation.

6. The prosthetic finger as claimed in claim 1 wherein the finger element is mounted pivotably on the carrier.

7. The prosthetic finger as claimed in claim 6, wherein the finger element is mounted pivotably about the first pivot axis.

8. The prosthetic finger as claimed in claim 6 wherein the finger element is coupled to the carrier via a toothed wheel or a toothed wheel segment.

9. The prosthetic finger as claimed in claim 1 wherein the finger element is mounted on a holder pivotably about a second pivot axis, and wherein the holder is secured on the carrier.

10. The prosthetic finger as claimed in claim 9, wherein the finger element comprises has a drive, and wherein the finger element is mounted on the holder pivotably by a motor.

11. The prosthetic finger as claimed in claim 9 wherein the first pivot axis and the second pivot axis are oriented crosswise.

12. The prosthetic finger as claimed in claim 1 wherein the drive element is mounted freely rotatably on the carrier.

13. The prosthetic finger as claimed in claim 1 wherein the coupling element is loaded in a direction of the drive element with a pretensioning force that permits a decoupling of the coupling element at a predefined torque.

14. The prosthetic finger as claimed in claim 1 wherein the carrier is assigned a position sensor or marker via which a position of the carrier relative to the chassis is detectable.

15. A prosthetic hand having a chassis and a prosthetic finger as claimed in claim 1.

16. The prosthetic hand as claimed in claim 15, wherein the motor drive is designed as an electric motor which drives an output element that engages with the drive element.

17. The prosthetic hand as claimed in claim 16, wherein the motor drive is coupled to the drive element via a gearing and/or a coupling.

* * * * *